United States Patent [19]

Schnaitter et al.

[11] Patent Number: 5,718,576
[45] Date of Patent: Feb. 17, 1998

[54] ORTHODONTIC ATTACHMENT DEVICE AND PIN

[75] Inventors: Dwight P. Schnaitter, Claremont; James D. Cleary, Glendora, both of Calif.

[73] Assignee: Minnesota Mining & Manufacturing Co., St. Paul, Minn.

[21] Appl. No.: 635,079

[22] Filed: Apr. 19, 1996

[51] Int. Cl.⁶ .................................................. A61C 7/26
[52] U.S. Cl. .................................................. 433/22; 433/19
[58] Field of Search .................................. 433/5, 17, 18, 433/19, 22, 20, 21

[56] References Cited

U.S. PATENT DOCUMENTS

| | | |
|---|---|---|
| 741,687 | 10/1903 | MacDowell . |
| 1,014,029 | 1/1912 | Angle .................... 433/21 |
| 2,959,856 | 11/1960 | Gurin . |
| 3,121,953 | 2/1964 | Asher .................... 433/5 |
| 3,137,941 | 6/1964 | Andrews ................. 433/5 |
| 3,158,934 | 12/1964 | Waldman . |
| 3,238,619 | 3/1966 | Brunson et al. . |
| 3,315,359 | 4/1967 | Moss . |
| 3,798,773 | 3/1974 | Northcutt . |
| 3,936,938 | 2/1976 | Northcutt ............... 433/21 |
| 3,997,970 | 12/1976 | Hodgson . |
| 4,038,754 | 8/1977 | Armstrong .............. 433/5 |
| 4,439,148 | 3/1984 | Hass ..................... 433/5 |
| 4,462,800 | 7/1984 | Jones .................... 433/19 |
| 4,525,143 | 6/1985 | Adams .................... 433/5 |
| 4,551,095 | 11/1985 | Mason .................... 433/19 |
| 4,583,944 | 4/1986 | Hanson ................... 433/22 |
| 4,708,646 | 11/1987 | Jasper ................... 433/19 |
| 4,849,032 | 7/1989 | Kawaguchi ............... 148/11.5 R |
| 5,306,142 | 4/1994 | Richards ................. 433/22 |
| 5,352,116 | 10/1994 | West ..................... 433/19 |
| 5,435,721 | 7/1995 | Vogt ..................... 433/19 |
| 5,562,445 | 10/1996 | DeVincenzo et al. ....... 433/19 |

OTHER PUBLICATIONS

"The correction of interarch malocclusions using a fixed force module", J.J. Jasper, DDS and James A. McNamara, Jr., DDS, PhD, *Am J Orthod Dentofac Orthop*, 1995; 108:641–50.

Reference Manual & Staff Training Guide for Adjustable Bite Corrector, Ortho Plus, Copyright 1994 Chap. 5, pp. 12–34.

Literature for Jasper Jumper™, American Orthodontics (date unknown).

Pp. 6–8 and 6–9, 1994 3M Unitek Catalog.

*Primary Examiner*—Cary E. O'Connor
*Attorney, Agent, or Firm*—James D. Christoff

[57] ABSTRACT

An orthodontic attachment device especially useful for coupling interarch and intra-arch appliances to an archwire includes an elongated wire that extends alongside the archwire. The wire is fixed to a crimpable connector having a passageway that receives the archwire. Wall portions surrounding the passageway are deformable in directions toward the passageway in order to non-rotatably couple the device to the archwire. In certain embodiments, a pin having an offset portion is connected to the appliance at a location remote from the attachment device in order to increase free play of the appliance when the patient's jaws are opened.

32 Claims, 7 Drawing Sheets

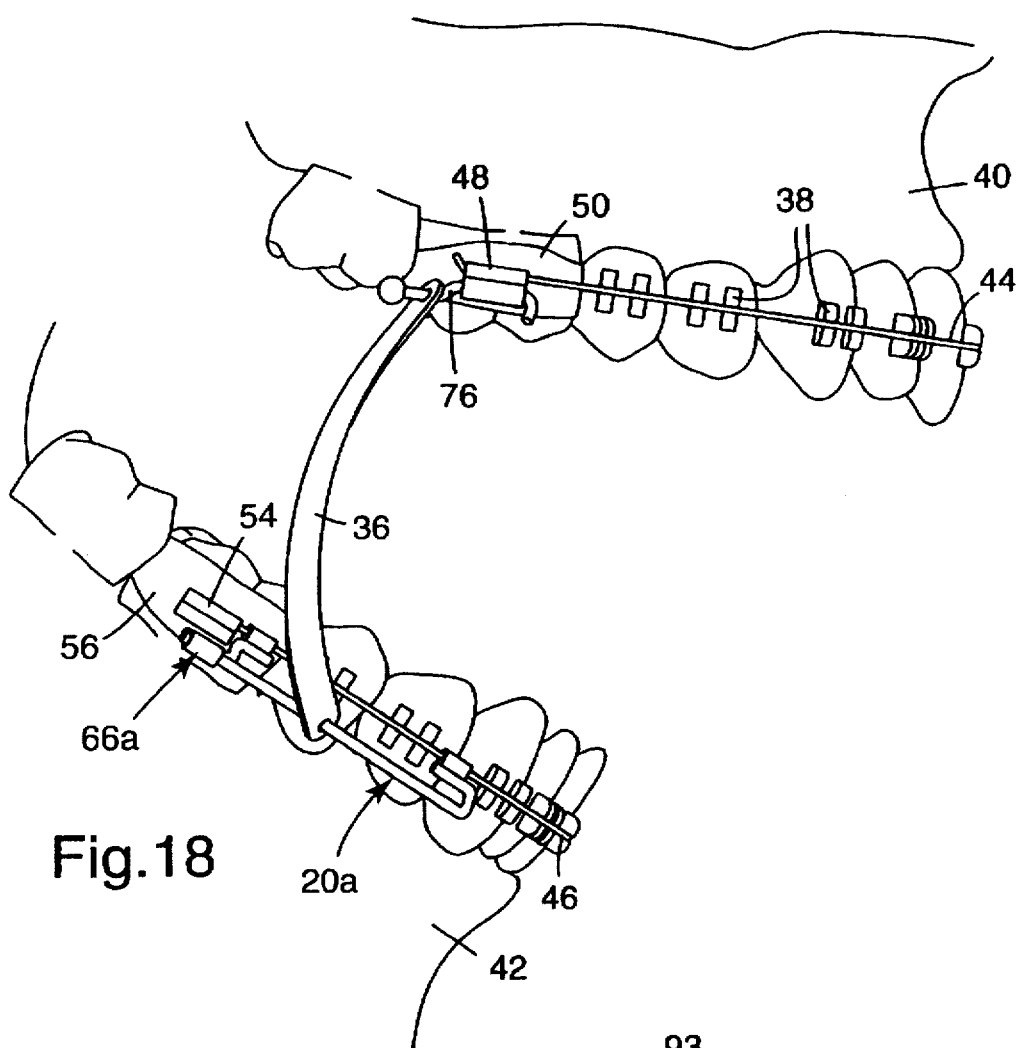
Fig.18
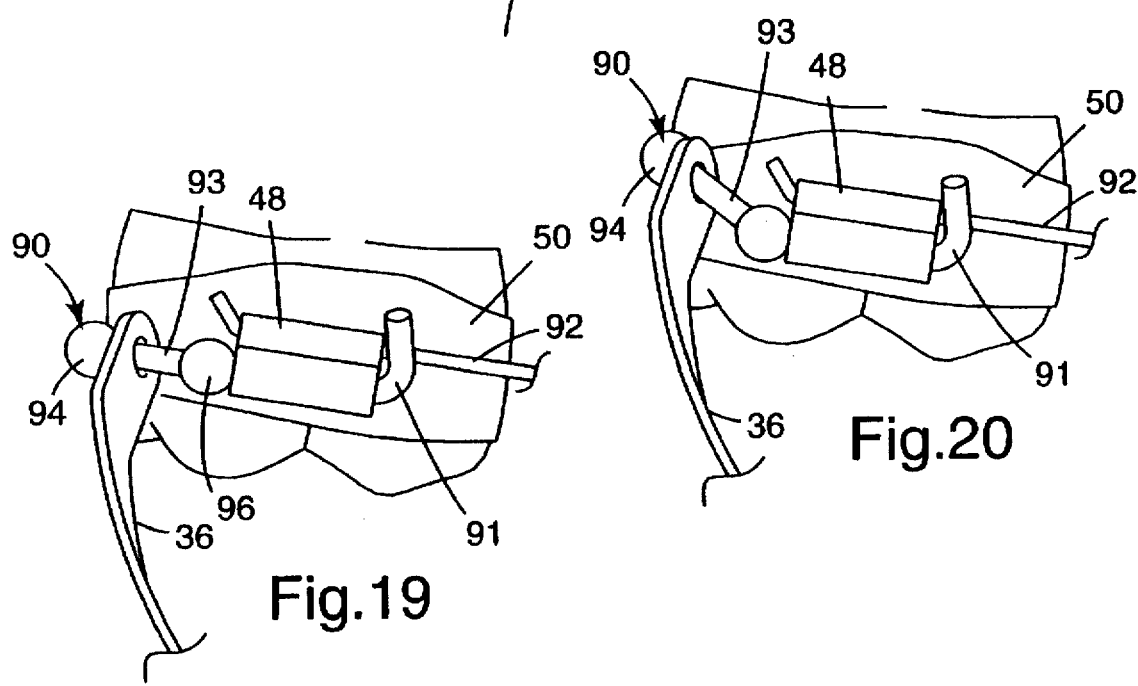
Fig.19
Fig.20

ORTHODONTIC ATTACHMENT DEVICE AND PIN

BACKGROUND OF THE INVENTION

1. Field of the Invention

This invention relates to an attachment device and a pin useful in orthodontic treatment. The invention is particularly useful for connecting intra-oral force modules and other appliances to a patient's upper or lower dental arch.

2. Description of the Related Art

Orthodontic treatment involves movement of malpositioned teeth to orthodontically correct positions. During treatment, tiny orthodontic appliances known as brackets are connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to molar teeth.

The orthodontic treatment of some patients includes correction of the alignment of the upper dental arch with the lower dental arch. For example, certain patients have a condition referred to as a Class II malocclusion wherein the lower dental arch is located an excessive distance rearward of the upper dental arch when the jaws are closed. Other patients may have an opposite condition referred to as a Class III malocclusion wherein the lower dental arch is located forward of the upper dental arch when the jaws are closed.

Orthodontic treatment of Class II and Class III malocclusions are commonly undertaken by movement of the upper dental arch as a single unit relative to movement of the lower dental arch as a single unit. To this end, pressure is often applied to each dental arch as a unit by applying pressure to the brackets, archwires or attachments connected to the brackets or archwires. In this manner, the Class II or Class III malocclusion can be corrected at the same time that the archwire and brackets are used to move individual teeth to desired positions.

In the past, Class II malocclusions were sometimes treated by connecting a pair of tension devices to both arches on opposite sides of the oral cavity. Examples of such devices include O-rings, a chain-type force module made of a number of integrally connected O-rings, or a coiled wire spring member. Such devices are used in tension to pull the jaws together in a direction along reference lines that extend between the points of attachment of the devices.

However, many of the tension devices used in treatment of a Class II malocclusions are removable by the patient for replacement when necessary and for cleaning of the teeth. Unfortunately, neglect of the patient to reinstall the devices seriously retards the progress of treatment. Poor cooperation from the patient can defeat timely achievement of the goals of an otherwise well-planned treatment program, resulting in an additional expenditure of time for both the patient and the orthodontist. Patient cooperation is often regarded as a common problem with adolescent patients.

A number of appliances that are fixed in place in the oral cavity during orthodontic treatment have been proposed in the past to overcome the problems of patient cooperation associated with removable tension devices. For example, U.S. Pat. Nos. 3,798,773, 4,462,800 and 4,551,095 disclose telescoping tube assemblies that urge the jaws toward positions of improved alignment. The assemblies are fixed to other orthodontic appliances such as brackets by the orthodontist, and thus problems of patient non-compliance are avoided.

Other orthodontic appliances that are fixed in place in the oral cavity for correcting Class II malocclusions are described in U.S. Pat. Nos. 4,708,646, 5,352,116 and 5,435,721. Such patents describe flexible members with end portion attachments for connection to the upper and lower jaws of a patient. The length of the member is selected such that the member is curved in an arch when the patient's jaws are closed. The inherent bias of the members toward a normally straight orientation provides a force that pushes one jaw forwardly or rearwardly relative to the other jaw.

The appliances described in U.S. Pat. Nos. 4,708,646, 5,352,116 and 5,435,721 have a generally elongated shape with openings near each end. The opening near the upper end is often connected to a pin having an enlarged head and a stem that is received in a passage of an appliance fixed to one of the patient's upper molar teeth. The opening near the lower end of the appliance is often received on a portion of the archwire that is attached to brackets on the patient's lower dental arch. In some instances, a stop such as a crimpable tube is fixed to the lower archwire on the mesial side of the lower end of each appliance, in order to limit movement of the lower end of the appliance along the archwire in a mesial direction. Other types of stops used in the past include a ball-shaped stop having a passageway receiving the archwire, where movement of the ball is limited by an adjacent bracket or by a bend in the archwire.

Preferably, the lower end of the appliances shown in U.S. Pat. Nos. 4,708,646, 5,352,116 and 5,435,721 slides freely in a distal direction along adjacent portions of the lower archwire when the patient's jaws are opened. If, for example, such sliding movement is hindered, repeated opening of the patient's jaws may fatigue the appliances, the associated pins or the lower archwire to such a degree that breakage may occur. In many instances, the orthodontist will remove brackets affixed to the patient's bicuspid teeth in order to increase the distance that the lower end of the appliances can slide along adjacent portions of the lower archwire.

However, removal of the bicuspid brackets to increase the range of sliding movement of the Class II correction appliances can retard treatment in some instances. For example, movement of such bicuspid teeth toward final desired positions for orthodontically correct occlusion is hindered during the time that the brackets are not in place. The bicuspid brackets can be rebonded to the tooth in order to guide movement of the associated bicuspid teeth once the Class II correction appliances are removed, but such a procedure is somewhat time consuming and may extend the overall length of treatment time.

Occasionally, orthodontists have attempted to avoid the problems noted above by connecting the lower end portion of Class II correction appliances to an auxiliary wire that extends alongside the lower archwire. In some instances, the auxiliary wires are soldered by the orthodontist on both ends to the lower archwire, and a ball stop is provided to engage the mesial side of the lower end portion of the appliance. However, such a practice is often considered unsatisfactory because the auxiliary wire must be soldered in place before the archwire is placed in the brackets, resulting in additional work for the orthodontist. Furthermore, the soldered joint may break apart in use and interrupt the progress of the treatment, and also necessitate a return visit by the patient to the orthodontist. In other instances, an auxiliary wire is fashioned by the orthodontist with a hook on one end for coupling to an archwire, and with either a hook on the other end for coupling to the archwire or a straight section for insertion into a buccal tube. However, it is somewhat time consuming for the orthodontist to fabricate such an auxiliary wire, and the results are often not entirely satisfactory.

SUMMARY OF THE INVENTION

The present invention overcomes the problems noted above by provision of an orthodontic attachment device for coupling an orthodontic appliance to an archwire. The device includes an elongated wire extending for a majority of its length along the archwire in a side-by-side relation. The device also includes a crimpable connector fixed to the wire. The crimpable connector has a passageway for receiving the archwire and wall portions at least partially surrounding the passageway. The wall portions are deformable in directions toward the passageway for nonrotatable connection to the archwire.

Another aspect of the present invention is directed toward an orthodontic assembly that comprises an orthodontic archwire, an orthodontic appliance having an opening, and an attachment device for coupling the appliance to the archwire. The attachment device includes an elongated wire and a crimpable connector coupled to the wire. The wire extends through the opening to slidably couple the appliance to the attachment device. The wire extends along the archwire in side-by-side relation. The crimpable connector has a passageway for receiving the archwire and deformable wall portions at least partially surrounding the passageway. The wall portions are crimped into an orientation of nonrotatable connection to the archwire.

The present invention also concerns an orthodontic pin comprising an elongated shank having a first section for rotatable reception within a passage of a buccal tube secured to a patient's tooth. The shank also includes a second section remote from the first section. The pin includes an enlarged head secured to the second section. The first section has a longitudinal axis, and the second section extends along an axis that is offset from the longitudinal axis.

Additionally, the present invention concerns an orthodontic pin comprising an elongated shank having a first section for rotatable reception within a passage of a butcat tube secured to a patient s tooth. The shank also includes a second section remote from the first section. The pin includes an enlarged head secured to the second section. The pin also includes a stop that is located between the first section and the second section.

Advantageously, the attachment device enables the lower end of a Class II correction appliance to freely travel a significant distance whenever the patient's jaws are opened without imposing undue stress on the appliance, the lower archwire or adjacent brackets. Moreover, no brackets normally need be removed for installation or use of the device or the appliance. The crimpable connector securely fixes the device to the archwire in an easy manner without the need for soldering and also prevents the attachment device from rotating about the longitudinal axis of the lower archwire, which might otherwise cause the appliance to catch or bind against another appliance in the oral cavity.

The offset configuration of the pin is an advantage, because the offset enables the positions of the Class II correction appliance to shift in the oral cavity a limited distance when the jaws are opened so that tensile stresses on the appliance and other associated orthodontic parts are reduced. For example, the shank of the pin may rotate relative to the buccal tube as the jaws are opened. As the pin rotates, the second end section pivots downwardly toward the patient's lower dental arch and enables the correction appliance to also move downwardly a corresponding distance. Downward movement of the appliance during the time when the patient's jaws are opened reduces tensile stresses on the appliance, and as a result the likelihood of breakage of the appliance, the archwire and adjacent brackets is reduced. The stop on the pin hinders sliding movement of the pin without preventing pivotal motion.

Other aspects and advantages of the invention are set out in the detailed description that follows and in the accompanying drawings.

BRIEF DESCRIPTION OF THE DRAWINGS

FIG. 18 is a view somewhat similar to FIG. 17 except that the jaws of the patient have been opened;

FIG. 19 is an enlarged fragmentary side elevational view somewhat similar to FIG. 17 but showing another embodiment of the pin of the present invention; and FIG. 20 is a view somewhat similar to FIG. 19 but in accordance with still another embodiment of the invention.

DETAILED DESCRIPTION OF THE PREFERRED EMBODIMENTS

Figure 1:
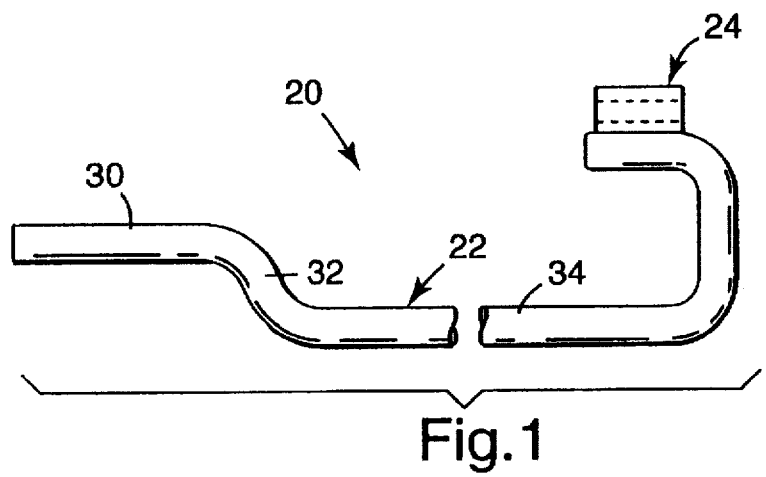
FIG. 1 is a fragmentary side elevational view of an orthodontic attachment device constructed in accordance with one embodiment of the present invention.
Figure 2:
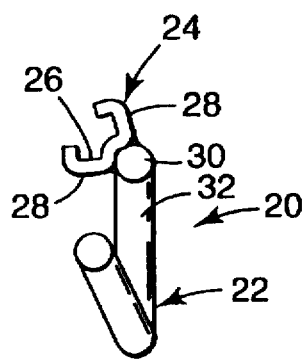
FIG. 2 is an end elevational view of the attachment device shown in FIG. 1.
Figure 3:
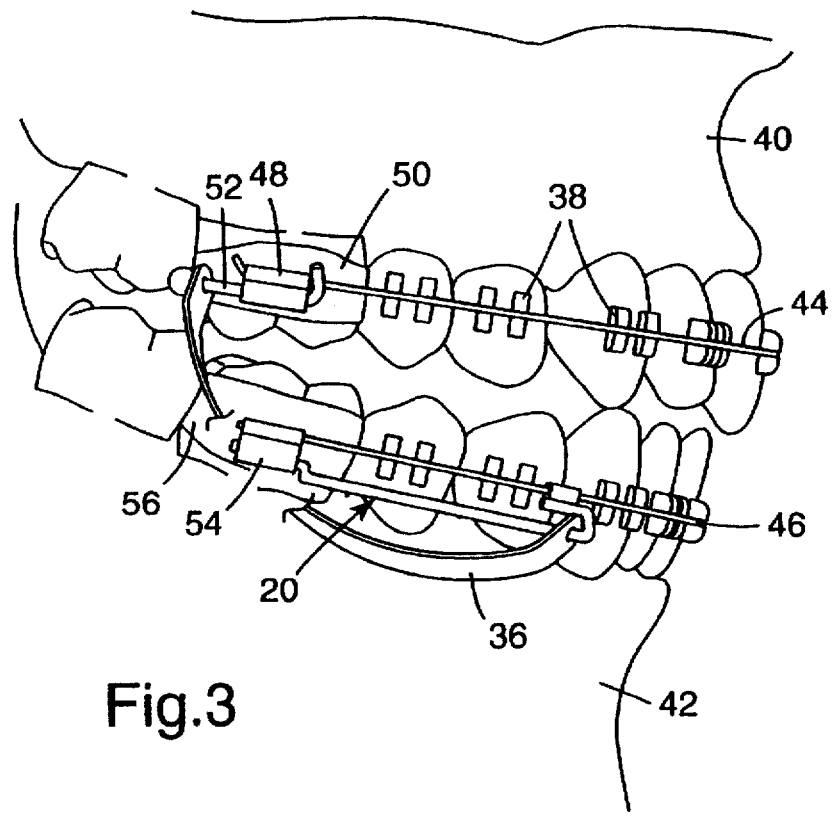
FIG. 3 is a reduced elevational view of an assembly connected for exemplary purposes to the upper and lower dental arches of a patient undergoing orthodontic treatment, wherein the assembly includes the attachment device shown in FIGS. 1 and 2.

An orthodontic attachment device 20 according to one embodiment of the invention is shown in FIGS. 1–3. The device includes an elongated section of wire 22 having a mesial (i.e., in a direction toward the middle of the patient's dental arch) end portion and a distal (i.e., in a direction away from the middle of the patient's dental arch) end portion. The mesial end portion of the wire 22 has a somewhat "j" shaped configuration, while the distal end portion of the wire 22 has an offset or somewhat "Z" shaped configuration.

The mesial end portion of the wire 22 is fixedly secured to a crimpable connector 24. As shown for example in FIGS. 1–2, the connector 24 includes a passageway 26 for receiving an archwire. The connector 24 also includes a pair of opposed, generally "C" shaped wall portions 28 that extend around and partially define the passageway 26. The passageway 26 has opposed open ends and a side that is initially open as illustrated in FIG. 2.

The wall portions 28 are deformable in directions toward the passageway 26 for non-rotatable connection to an archwire. When the wall portions 28 are moved toward each other, the passageway 26 is generally closed along its side and preferably has a transverse cross-sectional area that is approximately equal to the transverse cross-sectional area of the archwire that is engaged. When, for example, the wall portions 28 are deformed toward each other by a pair of pliers or other similar tool, the wall portions tightly and securely grip the archwire in such a fashion that the device 20 cannot rotate relative to the archwire in reference planes transverse to the longitudinal axis of the archwire.

The distal end portion of the wire 22 includes a distal end section 30 and an offset section 32. The distal end section 30 extends along a reference axis that is generally parallel to but offset from the longitudinal axis of a middle portion 34 of the wire 22. The distal end section 30 may have either a round, square or rectangular configuration in reference planes perpendicular to its longitudinal axis. The offset section 32 and the bottom (or mesial-most) section of the "j"-shaped mesial end portion both extend at an angle of approximately 90 degrees relative to the longitudinal axis of the middle portion 34 as shown in FIG. 1, and also extend at an acute angle relative to each other as shown in FIG. 2.

The wire 22 and the connector 24 may be made of any one of a number of non-corrosive metal alloys suitable for use in orthodontic treatment. An example of a suitable material is type 302 stainless steel. The wire 22 may be a drawn wire, or alternatively may be made by a casting, machining or metal injection molding process. The connector 24 may be fixed to the wire 22 by a brazing process although other methods are, of course, possible.

FIG. 3 illustrates for exemplary purposes the use of the attachment device 20 in orthodontic treatment. In this instance, the device 20 is shown in use in combination with an appliance 36 that is made of a unitary, resilient thin band of material (such as that described in the aforementioned U.S. Pat. No. 5,435,721) in order to correct a Class II malocclusion. The disclosure of U.S. Pat. No. 5,435,721 is incorporated by reference herein.

In FIG. 3, a set of slotted orthodontic brackets 38 is schematically shown. The brackets 38 are connected to teeth of an upper jaw 40 and a lower jaw 42 of the patient. An upper archwire 44 extends through slots of the brackets 38 connected to the patient's upper jaw 40, while a lower archwire 46 extends through slots of the brackets 38 connected to the patient's lower jaw 42. Although not shown, a wire or elastic ligature extends around tie wings of each of the brackets 38 in order to secure the archwires 44, 46 in respective slots of the brackets 38.

In FIG. 3, a buccal tube 48 is secured to a band 50 that surrounds the patient's upper right first molar tooth. The buccal tube 48 includes a first passage that receives one end of the upper archwire 44. The buccal tube 48 also has a second passage that receives a pin 52.

The pin 52 has a stem that is connected on its distal end to an enlarged head. The stem is threaded through an opening in an upper end portion of the appliance 36. An outermost mesial end section of the stem is bent by the orthodontist as shown in FIG. 3 in order to retain the pin 52 in the second passage of the buccal tube 48.

The wire 22 of the attachment device 20 is threaded through an opening in a lower portion of the appliance 36. As illustrated, the connector 24 is crimped onto a section of the lower archwire 46 between, for example, the patient's lower right cuspid tooth and lower right first bicuspid tooth. Of course, other attachment locations are also possible. Advantageously, the connector 24 enables the orthodontist to select the desired attachment location as needed and after the archwire 46 is installed in the brackets 38.

The distal end portion of the wire 22 is received in a passage of a buccal tube 54 that is fixed to a molar band 56. The band 56 in this instance encircles the patient's lower right first molar tooth. The buccal tube 54 also has a second passage that receives the distal right end of the lower archwire 46. In FIG. 3 (as well as in FIGS. 8 and 11 that follow), a middle portion of the appliance 36 is broken away to better illustrate the buccal tube 54 and adjacent components.

Preferably, the transverse cross-sectional area of the wire 22 is greater than the transverse cross-sectional area of the lower archwire 46 in order to better withstand forces imposed by the appliance 36 during movement of the patient's jaws 42, 44. For example, the wire 22 may have a circular cross-sectional configuration with a diameter of 0.032 inch (0.8 mm), while the lower archwire 46 may have a circular cross-sectional configuration with a diameter of approximately 0.022 inch (0.5 mm). Other sizes are, of course, possible.

The wire 22, or at least the distal end portion of the wire 22, may also have a transverse cross-sectional configuration that is square or rectangular instead of circular. For example, if the buccal tube 54 has an auxiliary passage that is square or rectangular instead of round, then the cross-sectional shape of the wire 22 may be modified accordingly in order to matingly fit into the auxiliary passage.

As can be appreciated, the attachment device 20 represents an inexpensive yet effective item which is easy to use and install without the need for removing brackets from the patient's teeth or soldering an auxiliary wire to an archwire. The overall length of the attachment device 20 can be readily modified as needed by cutting the distal end portion of the wire 22 to an appropriate length in order to avoid protrusion of the distal end of the wire 22 rearwardly from the lower buccal tube 54. The device 20 also serves to rigidly and strengthen the adjacent assembly of the brackets 38 and the archwire 46 on the patient's lower jaw 42.

In use, the wire 22 provides a sliding connection between the appliance 36 and the lower archwire 46 without interference with the brackets 38 that are connected to the patient's lower jaw 42. Since the connector 24 is non-rotatably secured to the lower archwire 46, the attachment device 20 remains fixed in place so that the likelihood of the attachment device 20 or the appliance 36 binding against other brackets, devices or appliances in the patient's oral cavity is substantially reduced. (Although not shown in the drawings, it is to be understood that the left side of the patient's oral cavity also contains an appliance and attachment device similar to the appliance 36 and attachment device 20 shown in FIG. 3.)

The "C"-shaped configuration of the mesial end portion of the wire 22 increases the distance that the lower end of the appliance 36 can travel in a mesial direction in contrast to other possible constructions. As shown in FIG. 3, when the jaws 40, 42 are substantially closed, the lower end of the appliance 36 bears against the bottom of the "C"-shaped mesial end portion as desired for correction of a Class II malocclusion. On the other hand, when the jaws 40, 42 are opened, the lower end of the appliance 36 can freely slide along the wire 22 in a distal direction without contacting brackets on the patient's lower bicuspid teeth, so that stresses on the appliance 36, the attachment device 20, the brackets 38 and other appliances in the patient's oral cavity are reduced.

Figures 4, 5:
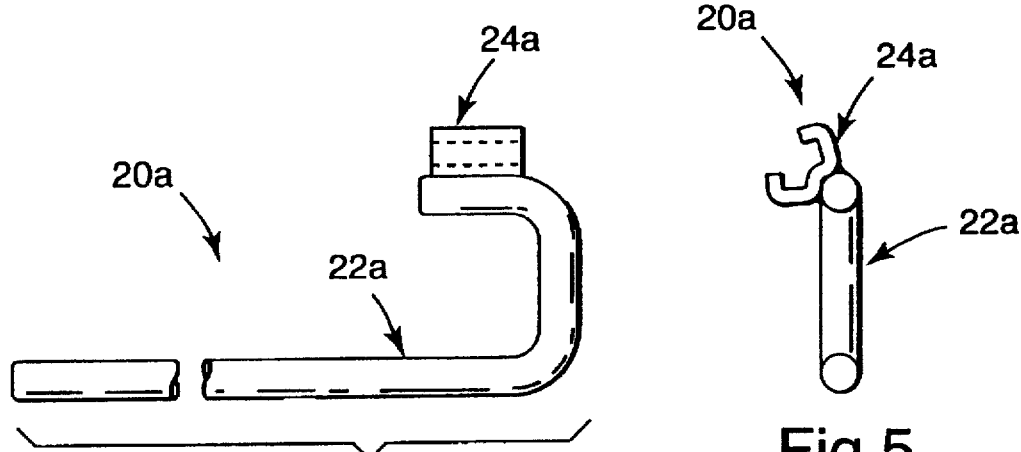
FIG. 4 is a fragmentary side elevational view of an attachment device constructed in accordance with another embodiment of the invention.
FIG. 5 is an end elevational view of the attachment device shown in FIG. 4.
Figures 6, 7:
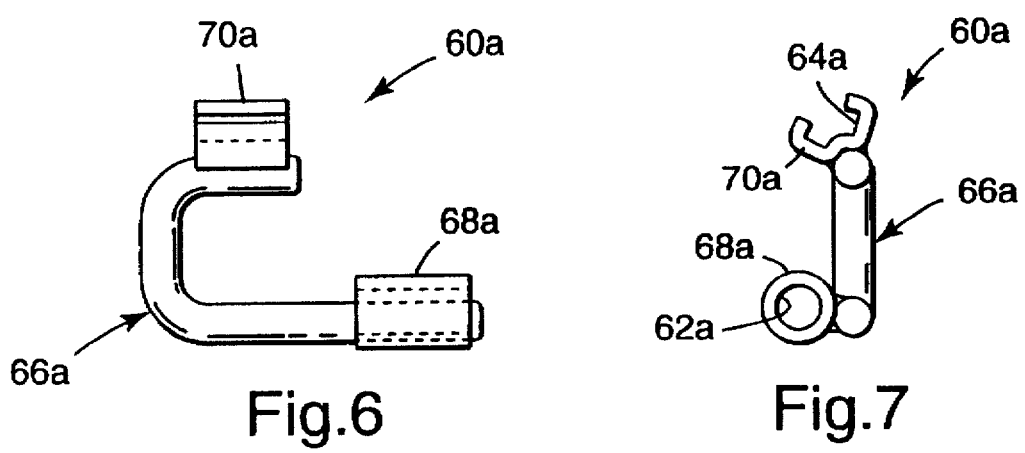
FIG. 6 is a side elevational view of a coupler adapted for use with the attachment device of FIGS. 4–5.
FIG. 7 is an end elevational view of the coupler illustrated in FIG. 6.

The orthodontic attachment device 20a that is illustrated in FIGS. 4 and 5 includes a connector 24a that is identical to the connector 24. The device 20a also includes a wire 22a that is identical to the wire 22, except that the distal end portion of the wire 22a has a straight configuration.

However, the device 20a also includes a coupler 60a having a first passage 62a and a second passage 64a. The coupler 60a also includes a body 66a that, in this embodiment, is a generally "C"-shaped section of relatively stiff wire. An example of a suitable wire is 0.034 inch (0.76 mm) diameter stainless steel wire having a circular transverse cross-sectional configuration The first passage 62a is located in a tubular member 68a that is brazed to a distal end portion of the body 66a. The second passage 64a is located within a member 70a that is brazed to a mesial end portion of the body 66a. The member 70a has deformable wall portions similar to the wall portions 28 that may be moved inwardly toward each other under the influence of pliers or another tool in order to securely grasp an archwire.

Figure 8:
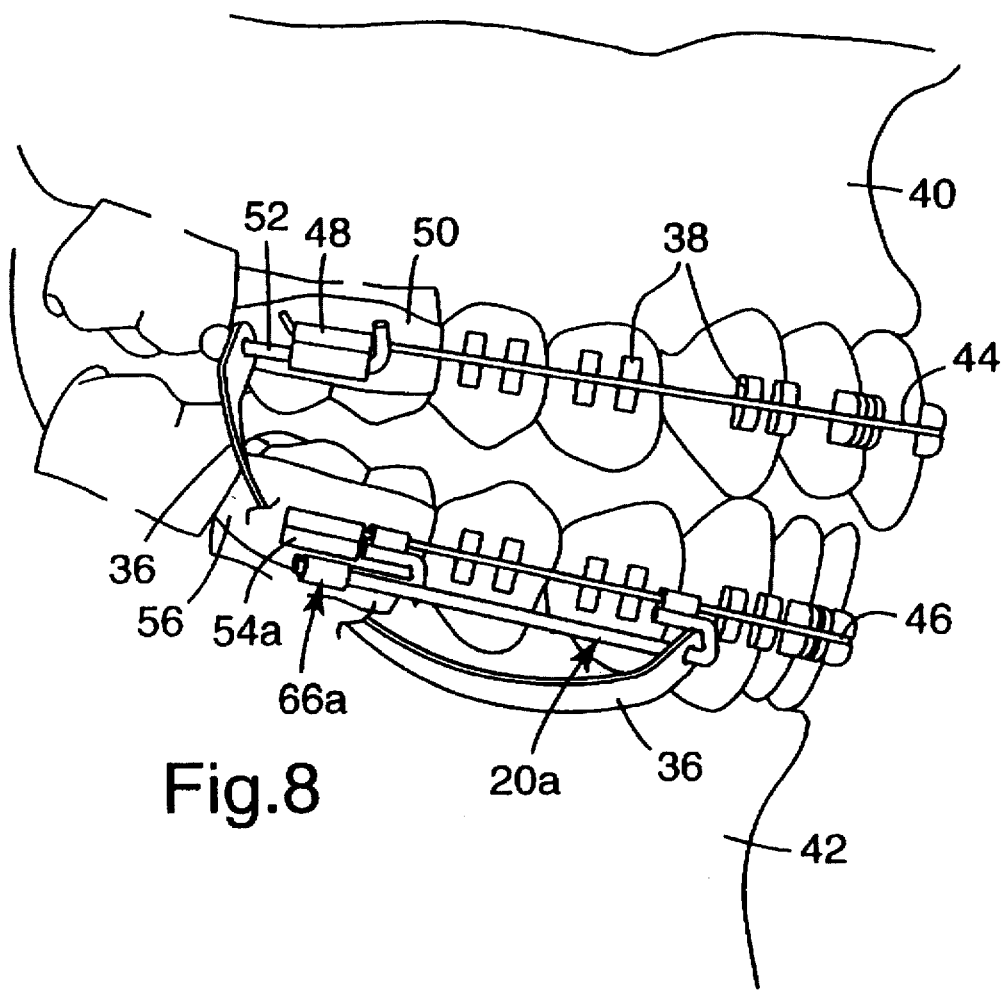
FIG. 8 is a reduced side elevational view of an orthodontic assembly according to another embodiment of the invention and shown for exemplary purposes in use in an oral cavity of a patient undergoing orthodontic treatment, wherein the assembly includes the attachment device depicted in FIGS. 4–5 and the coupler illustrated in FIGS. 6–7.

FIG. 8 is an illustration for exemplary purposes of the attachment device 20a when used in connection with the coupler 60a for a patient undergoing orthodontic treatment. In FIG. 8, elements denoted with numerals lacking the "a" designation are the same as like-numbered elements described above in connection with FIG. 3, and as such a detailed description of those elements need not be repeated.

As illustrated in FIG. 8, the member 70a of the coupler 60a is crimped onto the lower archwire 46 at a location near the mesial side of a lower buccal tube 54a. The distal end portion of the wire 22a is inserted into the first passage 62a of the coupler 60a after being cut as needed to the proper length. In addition, the connector 24a is crimped onto the lower archwire 46 at a location between the patient's lower right cuspid and first bicuspid tooth.

Although both the first passage 62a and the transverse crosssectional configuration of the distal end portion of the wire 22a are circular and hence might otherwise be swivelable relative to each other, the crimped connector 24a and the crimped member 70a essentially preclude swiveling movement of the device 20a including the coupler 60a about the longitudinal axis of the lower archwire 46. Consequently, the device 20a serves as a fixed, secure connection that slidably couples the lower end of the appliance 36 to the patient's lower jaw 42.

Optionally, the buccal tube 54a may differ from the buccal tube 54 in that the buccal tube 54a may have only a single passage for receiving the lower archwire 46 and may lack an auxiliary passage such as might also be used for lip bumpers or the like. Consequently, by use of the coupler 60a, the orthodontist need not replace the lower buccal tube 54a with another buccal tube having an auxiliary passage when use of a correction appliance such as appliance 36 is desired.

Figure 9:
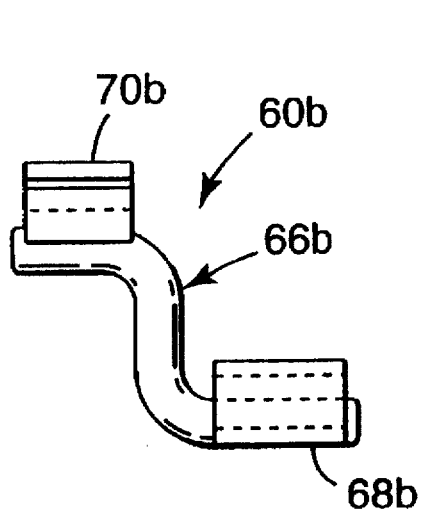
FIG. 9 is a side elevational view of a coupler constructed in accordance with another embodiment of the present invention.
Figure 10:
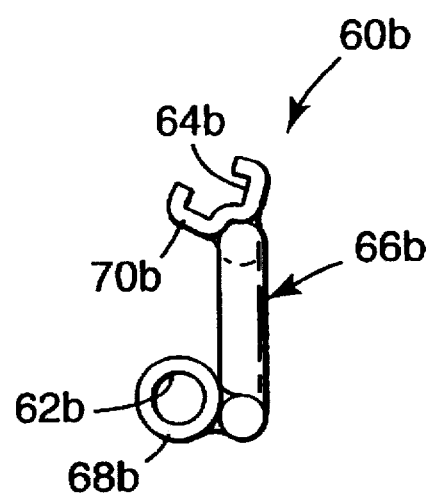
FIG. 10 is an end elevational view of the coupler depicted in FIG. 9.
Figure 11:
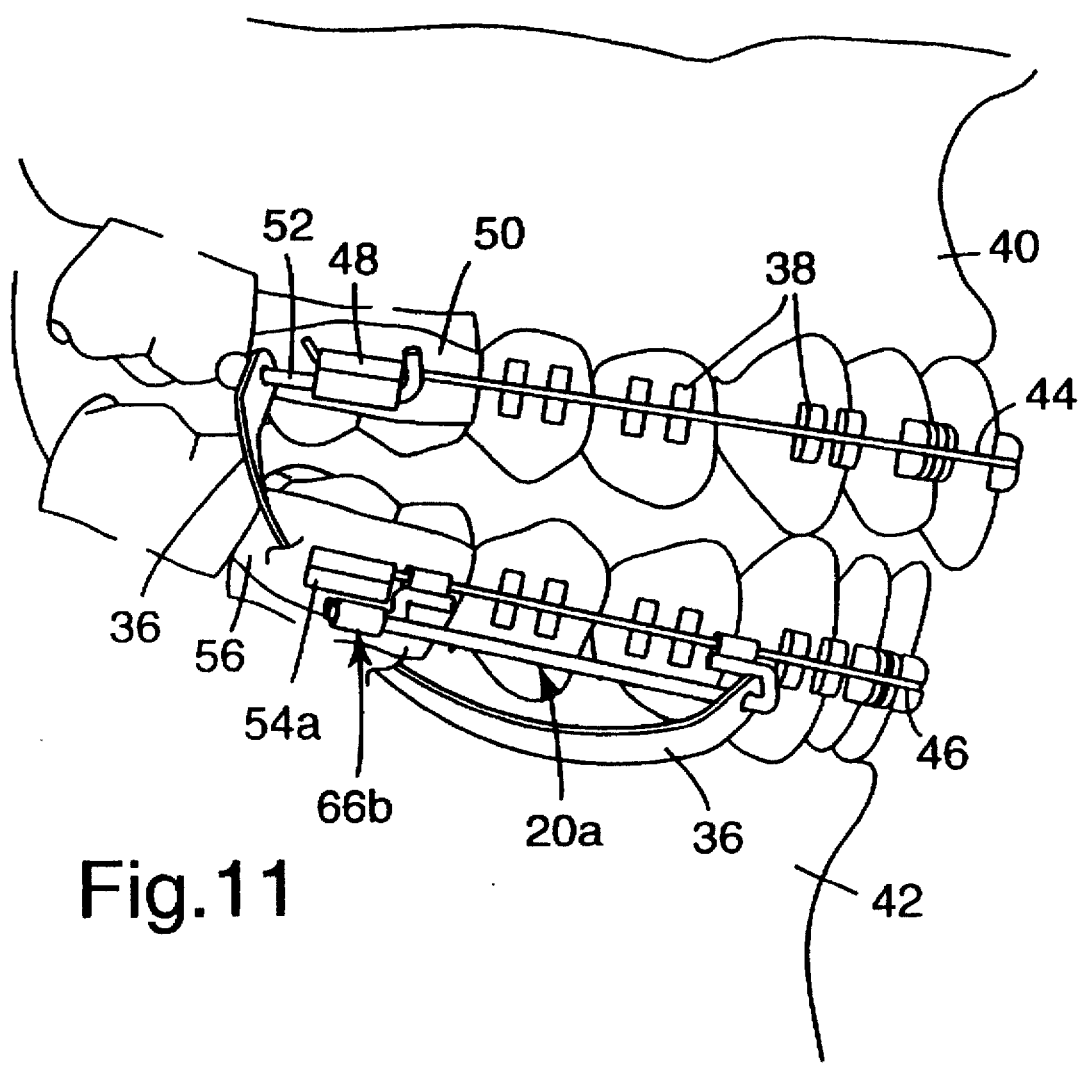
FIG. 11 is a view somewhat similar to FIG. 8 except showing the coupler device that is illustrated in FIGS. 9 and 10 in place of the coupler device depicted in FIGS. 6–7.
Figure 12:
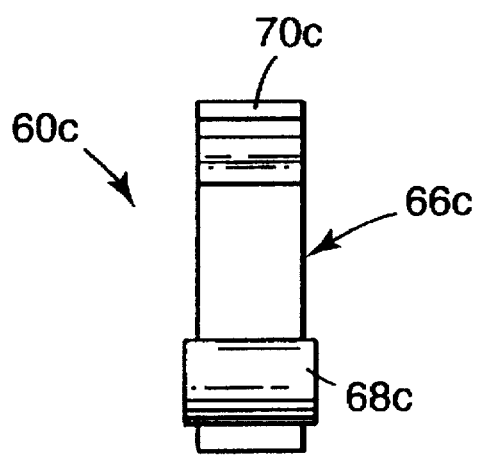
FIG. 12 is a side elevational view of a coupler constructed in accordance with yet another embodiment of the invention.
Figure 13:
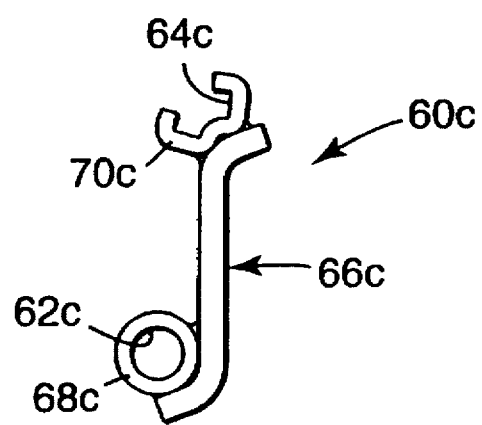
FIG. 13 is an end elevational view of the coupler shown in FIG. 12.

Another embodiment of the invention is illustrated in FIGS. 9-11. In FIGS. 9 and 10, a coupler 60b includes a member 68b with a first passage 62b and a member 70b with a second passage 64b. The members 68b, 70b are identical to the members 68a, 70a respectively and thus a detailed description of both need not be repeated.

The coupler 60b also includes a body 66b that in this embodiment is made of the same material as the body 66a and is connected to the members 68b, 70b in a manner similar to the manner of connection of the body 66a to the members 68a, 70a. However, in this embodiment, the body 66b has an offset, or generally "Z"-shaped configuration as can be best appreciated by reference to FIG. 9.

FIG. 11 is an illustration for exemplary purposes of the coupler 60b when used in place of the coupler 60a in conjunction with other elements of the attachment device 20a shown in FIGS. 4 and 5. In FIG. 11, numerals that are the same as numerals in FIGS. 4-5 and 8 refer to identical elements, and as such a detailed description of those elements need not be repeated.

The coupler 60b is connected to the lower archwire 46 in a manner similar to that described in connection with the coupler 60a in FIG. 8. Similarly, the distal end portion of the attachment device 20a is connected to the coupler 60b in FIG. 11 in a manner identical to the attachment of the same distal end portion to the coupler 60a. As can be appreciated by reference to FIG. 11, the generally "Z"-shaped configuration of the body 66b provides an advantage in that under some circumstances the lower end of the appliance 36 may move further in a distal direction when the jaws 40, 42 are opened in comparison to the possible range of travel of the lower end of the appliance 36 in the embodiment shown in FIG. 8.

Another embodiment of the invention is illustrated in FIGS. 19. and 13, and concerns a coupler 60c having a member 68c with a first passage 62c and a member 70c with a second passage 64c. The members 68c, 70c are identical to the members 68a, 70a.

However, the coupler 60c includes a body 66e that is somewhat different than the body 66a or body 66b. The body 66c is a generally "S"-shaped bar section of metallic stock such as type 304 stainless steel. The members 68c, 70c are brazed to the body 66c. The body 66c may be cut and formed from initially flat stock by a stamping operation.

Figure 14:
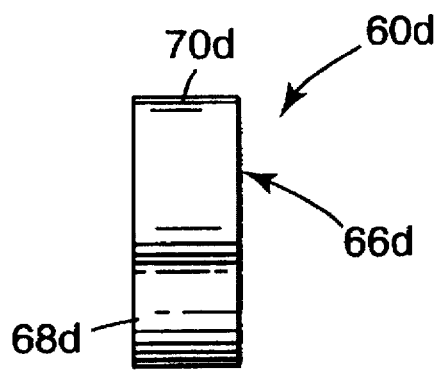
FIG. 14 is a side elevational view of a coupler constructed according to still another embodiment of the invention.
Figure 15:
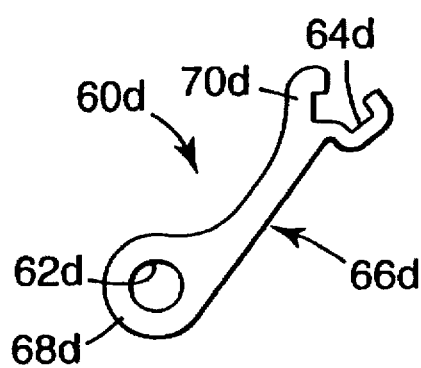
FIG. 15 is an end elevational view of the coupler depicted in FIG. 14.

The embodiment of the invention that is shown in FIGS. 14 and 15 concerns a coupler 60d made of a unitary section of metallic material. For example, the coupler 60d may be made by a casting, machining or metal injection molding process. The coupler 60d includes member portion 68d having a first passage 62d that is similar to the passage 62a and a member portion 70d having a second passage 64d that is similar to the second passage 64a.

Wall portions of the coupler 60d surrounding the second passage 64d are deformable in an inwardly direction toward each other. As a consequence, the wall portions can be crimped into an orientation of secure, non-rotatable connection to an archwire such as the lower archwire 46.

Figure 16:
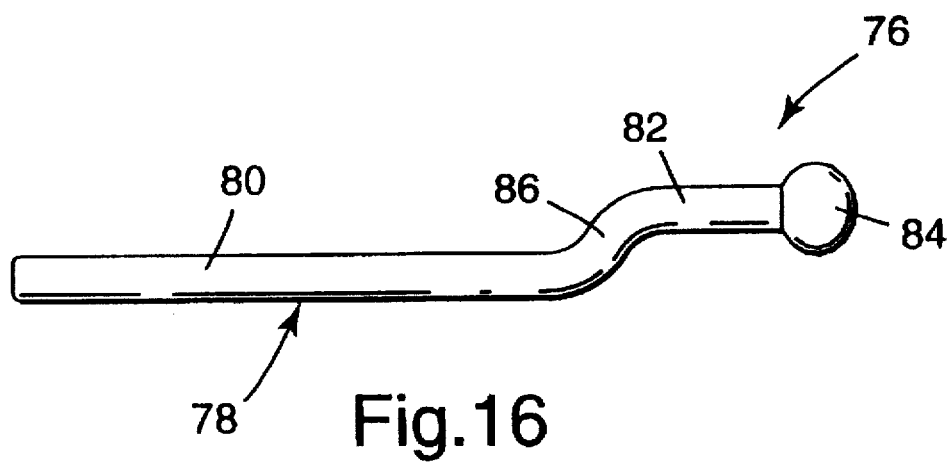
FIG. 16 is an elevational view of an orthodontic pin of the invention.
Figure 17:
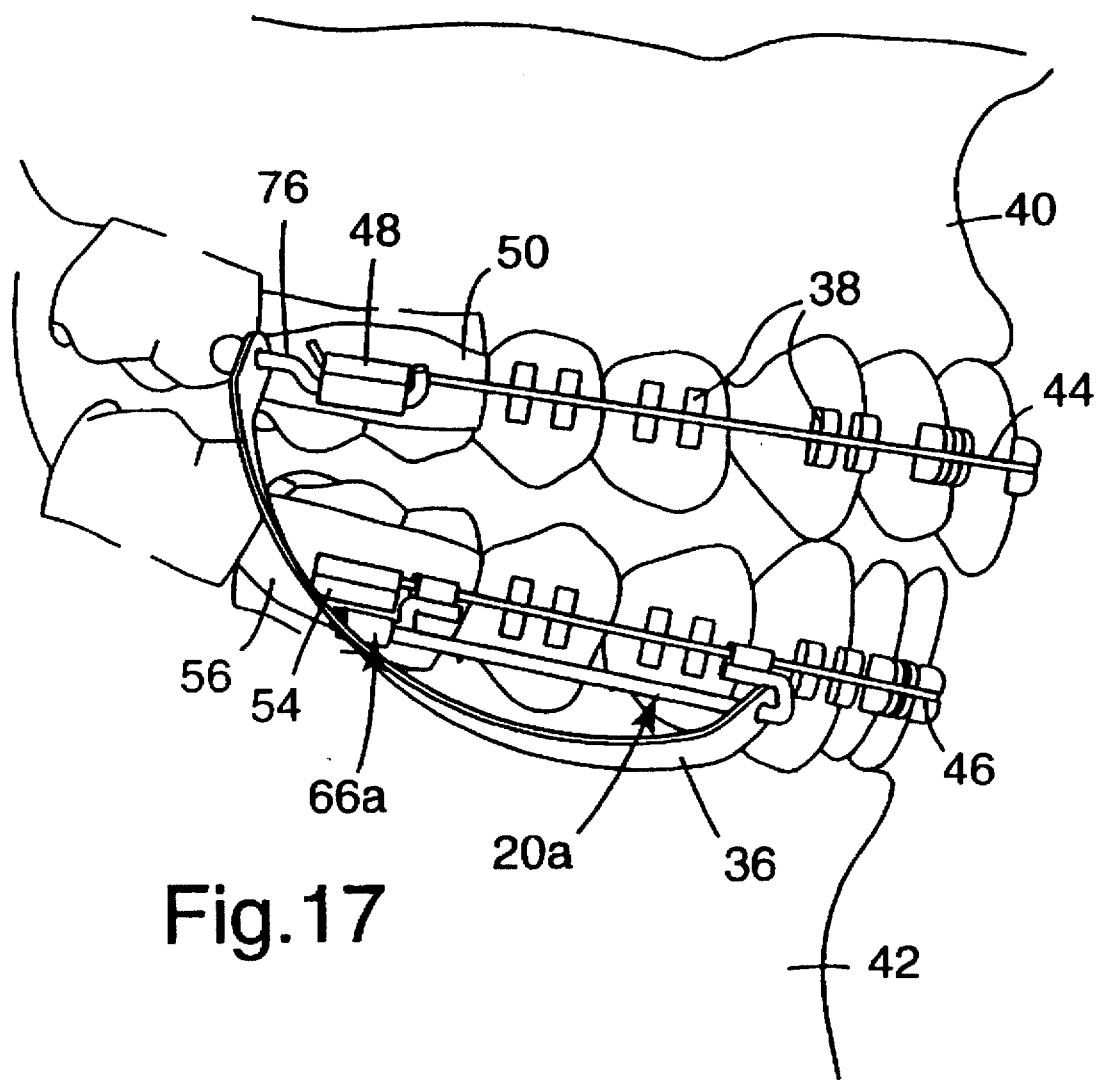
FIG. 17 is a reduced side elevational view of an orthodontic assembly shown for exemplary purposes in an oral cavity of a patient undergoing orthodontic treatment, wherein the assembly includes the pin illustrated in FIG. 16.

Another aspect of the invention, which is especially useful in combination with the attachment device 20, 20a and the appliance 36, is an orthodontic pin 76 that is illustrated in FIGS. 16–18. The pin 76 alone is shown in FIG. 16, and includes an elongated shank 78 having a first section 80 for rotatable reception within a passage of a butcat tube secured to a patient's tooth. The shank 78 also includes a second section 82 remote from the first section 80.

The pin 76 has an enlarged generally spherical head 84 secured to the distal end of the second section 82. Preferably, the head 84 is integrally connected to the shank 78, and the pin 76 is made of a non-corrosive non-toxic material such as 300 series stainless steel. The pin 76 may be made by a casting, machining, cold-heading or metal injection molding process.

The second section 82 of the pin 76 is offset from the first section 80. In the embodiment shown, the second section 82 extends along an axis that is parallel to but offset from the longitudinal axis of the first section 80. The second section 82 is connected to the first section 80 by an intermediate section 86 that extends along an axis that is preferably oriented 90° or less relative to the longitudinal axes of the first section 80 and the second section 82 respectively.

Preferably, the shank 78 is made of a wire section having a diameter of approximately 0.04 inch (1 mm). Optionally, an outermost end region of the first section 80 has a reduced cross-sectional area that is smaller in area than remaining transverse cross-sectional areas of the shank 78, so that the end region can be readily bent by the orthodontist as needed after insertion of the first section 80 into an appliance.

Referring now to FIGS. 17 and 18, the pin 76 is shown for exemplary purposes as it might be used for a patient undergoing orthodontic treatment. In FIGS. 17 and 18, numerals that are the same as the numerals shown in FIG. 11 refer to identical elements, and as such a detailed description of those elements need not be repeated. As used herein, "buccal tube" shall mean any appliance that is secured to a molar tooth of the patient.

Referring initially to FIG. 17, installation of the pin 76 is carried out by threading the shank 78 through the upper opening of the appliance 36 and then inserting the first section 80 of the shank 78 into an auxiliary passage of the upper buccal tube 48. Next, and as shown in the drawings, the outermost end region of the first section 80 is bent in an arc by a pliers or other tool, until such time as such outer end region extends at an angle of approximately 90° relative to the longitudinal axis of remaining portions of the first section 80. The bent outer end region serves to retain the pin 76 in the butcat tube 48 and the intermediate section 86 serves as a stop to limit longitudinal sliding movement of the pin 76 relative to the butcat tube 48.

When the patient's jaws 40, 42 are generally closed as shown in FIG. 17, the shank 78 tends to move toward the orientation shown in FIG. 17 wherein the second section 82 is located upwardly of the first section 80 and is essentially as remote as possible from the lower dental arch 42. In such an orientation, the upper end of the appliance 36 bears against the head 84 while the lower end of the appliance 36 bears against the bottom of the mesial end portion of the wire 22 that is closest to the center of the patient's lower dental arch 42.

However, when jaws 40, 42 are opened such as is shown in FIG. 18, the shank 78 swivels in the auxiliary passage of the upper buccal tube 48 as the appliance 36 moves closer toward a straight orientation. The pivotal movement of the shank 78 relative to the upper buccal tube 48 enables the second section 82 to move somewhat closer to the lower jaw 42, so that additional space is provided for free movement of the appliance 36 as it returns to its normally straight configuration before imposing tensile stresses on the pin 76 and the wire 22. As the jaws 40, 42 are opened, the lower end of the appliance 36 also slides in a distal direction along the wire 22 to facilitate opening of the jaws 40, 42 without undue hindrance.

For example, if the first section 80 is offset from the second section 82 a distance of 2.5 mm, such offset distance provides a total of 5 mm of additional space for free movement of the appliance 36 as the pin 76 rotates through an arc of 180°. While such a dimension may at first blush appear relatively small, the additional space may greatly reduce tensile stresses on the pin 76, the upper buccal tube 48, the device 20a, the lower archwire 46 and the brackets 38 in the vicinity of the attachment device 20a, such that the likelihood of breakage of such elements and debonding of such brackets 38 from the associated teeth is greatly reduced.

A pin 90 that is shown in FIG. 19 is an alternative embodiment of the pin 76 described above. The pin 90 includes an elongated shank 92 with a first section 91 and a second section 93. An enlarged spherical head 94 is preferably integrally connected to the shank 92. The head 94 and the shank 92 are preferably constructed of the materials set out above in connection with the pin 76.

The pin 90 also includes a ball stop 96 that is fixedly secured to the shank 92 at a location between the first section 91 and the second section 93 by a crimping operation. Before the ball stop 96 is secured in place, the shank 92 is threaded through the opening in the upper portion of an appliance such as the appliance 36 described above. Preferably, the ball stop 92 is spaced from the head 94 a distance in the range of about 2 mm to about 5 mm, and the upper end of the appliance 36 is freely slidable on the second section 93 of the shank 92.

The first section 91 is initially straight, and is bent by the orthodontist after insertion into the buccal tube 48. During use, the ball stop 96 limits the range of sliding movement of the shank 92 in the buccal tube 48, while also enabling the appliance 36 to slide along the second section 93 without hindrance as may occur, for example, when the patient's jaws are opened and closed. Although the stop 96 shown in the drawings has a generally spherical configuration, it should be understood that other types of stops are also possible so long as the stop is effective in limiting sliding movement of the pin and also enables the appliance (such as appliance 36) to slide along a portion of the shank of the pin. Moreover, the stop could be integral or initially separate from the shank.

FIG. 20 shows the pin 90 in an orientation where the shank 92 has been bent such that the longitudinal axis of the second section 93 extends at an acute angle relative to the longitudinal axis of the portion of the first section 91 that is within the buccal tube 48. Such construction is an advantage, in that the pin 90 can swivel within the buccal tube 48 about the longitudinal axis of the first section 91 in a manner similar to swiveling movement of the shank 78 as discussed above. Such swiveling motion provides additional space for movement of the appliance 36 so that the likelihood of imposing undue tensile stresses on the pin 90, the buccal tube 48 and other components is significantly reduced. Of course, other shank configurations are also possible, such as the offset configuration illustrated in FIGS. 16–18.

Those individuals skilled in the art may recognize that a variety of modifications and additions to the presently preferred embodiments are possible without departing from the spirit of our invention. Furthermore, the attachment device 20, 20a and the pin 76 may be used in other applications or with appliances (such as Herbst, Class III correction devices, intra-arch devices and other appliances) other than the appliance 36. As such, the invention shall not be deemed limited by the embodiments described in detail above, but only be a fair reading of the claims that follow along with their equivalents.

We claim:

1. An orthodontic attachment device for coupling an orthodontic appliance to an elongated archwire comprising:

an elongated wire extending for a majority of its length along the archwire in side-by-side relation; and a crimpable connector immovably fixed to said wire, said crimpable connector having a passageway larger than the archwire for receiving the archwire and having opposed wall portions at least partially surrounding said passageway, said passageway having opposed open ends and a side, said side being initially open to receive the archwire in a direction laterally of the archwire's length, said wall portions being deformable in directions toward said passageway for non-rotatable connection to the archwire.

2. The attachment device of claim 1 wherein said wire has a distal end portion having a circular transverse cross-sectional configuration.

3. The attachment device of claim 1 wherein said wire has a distal end portion having a rectangular transverse cross-sectional configuration.

4. The attachment device of claim 1 wherein said wire has a distal end portion with an offset section for facilitating entry into a buccal tube.

5. An orthodontic attachment device for coupling an orthodontic appliance to an archwire comprising:

an elongated wire extending for a majority of its length along the archwire in side-by-side relation;

a crimpable connector immovably fixed to said wire, said crimpable connector having a passageway larger than the archwire for receiving the archwire and having wall portions as least partially surrounding said passageway, said wall portions being deformable in directions toward said passageway for non-rotatable connection to the archwire, wherein said wire has a mesial end portion and a distal end portion, wherein said connector is fixed to said mesial end portion; and a buccal tube having a passage receiving said distal end portion.

6. The attachment device of claim 5 wherein said buccal tube is a lip bumper tube.

7. An orthodontic attachment device for coupling an orthodontic appliance to an archwire comprising:

an elongated wire extending for a majority of its length along the archwire in side-by-side relation; and a crimpable connector fixed to said wire, said crimpable connector having a passageway for receiving the archwire and wall portions at least partially surrounding said passageway, said wall portions being deformable in directions toward said passageway for non-rotatable connection to the archwire, and wherein said wire has an overall generally "J"-shaped configuration.

8. An orthodontic assembly comprising:

an orthodontic archwire;

an orthodontic appliance having an opening; and an attachment device for coupling said appliance to said archwire, said attachment device including an elongated wire and a crimpable connector immovably fixed to said wire, said wire extending through said opening to slidably couple said appliance to said attachment device, said wire extending along said archwire in side-by-side relation, said crimpable connector having a passageway for receiving said archwire and deformable wall portions at least partially surrounding said passageway, said wall portions being crimped into an orientation of non-rotatable connection to said archwire.

9. The assembly of claim 8, wherein said archwire is a certain transverse cross-sectional area, and wherein said wire has a transverse cross-sectional area that is larger than said certain cross-sectional area.

10. The assembly of claim 8, wherein said wire extends along said archwire in parallel relation thereto.

11. The assembly of claim 8, wherein said wire has a distal end portion; and including a coupler for connecting said distal end portion to said archwire, said coupler including a first passage for receiving said distal end portion and a second passage for receiving said archwire.

12. The assembly of claim 11, wherein said coupler includes crimpable wall portions next to said second passage.

13. The assembly of claim 12, wherein said wall portions are non-rotatably connected to said archwire.

14. The assembly of claim 11, wherein said distal end portion of said wire is rotatably received in said first passage of said coupler.

15. The assembly of claim 11, wherein said coupler is made of a single, unitary body.

16. The assembly of claim 11, wherein said coupler includes a body having a generally "C"-shaped configuration.

17. The assembly of claim 8, wherein said appliance has a second opening; and including a pin having a shank with a first section for rotatable reception within a passage of an appliance secured to a patient's tooth and a second section remote from said first section, said second section extending through said second opening of said appliance, said pin including an enlarged head secured to said second section, said first section having a longitudinal axis, said second section extending along an axis that is offset from said longitudinal axis.

18. The assembly of claim 17, wherein said first section and said second section extend in generally parallel directions.

19. The assembly of claim 17, wherein said first section has a certain transverse cross-sectional area, and wherein said second section has a transverse cross-sectional area that is larger than said certain cross-sectional area.

20. An orthodontic assembly comprising:

an orthodontic archwire;

an orthodontic appliance having an opening; and an attachment device for coupling said alliance to said archwire, said attachment device including an elongated wire and a crimpable connector coupled to said wire, said wire extending through said opening to slidably couple said appliance to said attachment device, said wire extending along said archwire in side-by-side relation, said crimpable connector having a passageway for receiving said archwire and deformable wall portions at least partially surrounding said passageway, said wall portions being crimped into an orientation of non-rotatable connection to said archwire, and wherein said attachment device has an overall generally "J"-shaped configuration.

21. An orthodontic assembly comprising:

an orthodontic archwire;

an orthodontic appliance having an opening;

an attachment device for coupling said appliance to said archwire, said attachment device including an elongated wire and a crimpable connector coupled to said wire, said wire extending through said opening to slidably couple said appliance to said attachment device, said wire extending along said archwire in side-by-side relation, said crimpable connector having a passageway for receiving said archwire and deformable wall portions at least partially surrounding said passageway, said wall portions being crimped into an orientation of non-rotatable connection to said archwire, and wherein said wire has a distal end portion; and a buccal tube having a passage receiving said distal end portion.

22. The assembly of claim 21, wherein said buccal tube is a lip bumper tube.

23. An orthodontic assembly comprising:

an orthodontic archwire;

an orthodontic appliance having an opening;

an attachment device for coupling said appliance to said archwire, said attachment device including an elongated wire and a crimpable connector coupled to said wire, said wire extending through said opening to slidably couple said appliance to said attachment device, said wire extending along said archwire in side-by-side relation, said crimpable connector having a passageway for receiving said archwire and deformable wall portions at least partially surrounding said passageway, said wall portions being crimped into an orientation of non-rotatable connection to said archwire, and wherein said wire has a distal end portion with an offset section for facilitating entry into a buccal tube.

24. An orthodontic assembly comprising:

an orthodontic archwire;

an orthodontic appliance having an opening;

an attachment device for coupling said appliance to said archwire, said attachment device including an elongated wire and a crimpable connector coupled to said wire, said wire extending through said opening to slidably couple said appliance to said attachment device, said wire extending along said archwire in side-by-side relation, said crimpable connector having a passageway for receiving said archwire and deformable wall portions at least partially surrounding said passageway, said wall portions being crimped into an orientation of non-rotatable connection to said archwire;

wherein said wire has a distal end portion; and a coupler for connecting said distal end portion to said archwire, said coupler including a first passage for receiving said distal end portion and a second passage for receiving said archwire, wherein said coupler includes a body having a generally "Z"-shaped configuration.

25. An orthodontic pin comprising an elongated shank having a first section for rotatable reception within a passage of an alliance secured to a patient's tooth and a second section remote from said first section, said pin including an enlarged head secured to said second section, said first section having a longitudinal axis said second section extending along an axis that is offset from said longitudinal axis, wherein said first section has a certain transverse cross-sectional area, and wherein said second section has a transverse cross-sectional area that is larger than said certain cross-sectional area.

26. The orthodontic pin of claim 25, wherein said first section and said second section extend in generally parallel directions.

27. The orthodontic pin of claim 25, wherein said head has a generally spherical shape.

28. The orthodontic pin of claim 25, wherein said first section has a generally circular transverse cross-sectional configuration.

29. An orthodontic pin comprising an elongated shank having a first section for rotatable reception within a passage of an appliance secured to a patient's tooth and a second section remote from said first section, said second section having a terminal end, said pin including an enlarged head secured to said terminal end of said second section, said pin including a stop located between said first section and said second section, and wherein said first section extends at an acute angle relative to the direction of extension of said second section.

30. The orthodontic pin of claim 29, wherein said first section has a generally circular transverse cross-sectional configuration.

31. An orthodontic pin comprising an elongated shank having a first section for rotatable reception with a passage of an alliance secured to a patient's tooth and a second section remote from said first section, said second section having a terminal end, said pin including an enlarged head secured to said terminal end of said second section, said pin including a stop located between said first section and said second section, and wherein said stop has a generally spherical shape.

32. The orthodontic pin of claim 31, wherein said first section and said second section extend in generally parallel directions.

* * * * *

UNITED STATES PATENT AND TRADEMARK OFFICE
CERTIFICATE OF CORRECTION

PATENT NO.: 5,718,576

DATED: February 17, 1998

INVENTOR(S): Dwight P. Schnaitter and James D. Cleary

It is certified that error appears in the above-identified patent and that said Letters Patent is hereby corrected as shown below:

Col. 12, line 57, "alliance" should read --appliance--.

Col. 14, line 11, "alliance" should read --appliance--.

Col. 14, line 43, "alliance" should read --appliance--.

Signed and Sealed this

Eighth Day of September, 1998

Attest:

BRUCE LEHMAN

Attesting Officer     Commissioner of Patents and Trademarks